United States Patent [19]
Gedeon et al.

[11] Patent Number: 4,538,605
[45] Date of Patent: Sep. 3, 1985

[54] ANESTHETIC APPARATUS

[75] Inventors: Andras Gedeon, Täby; Leif Odselius, Upplands Väsby, both of Sweden

[73] Assignee: Gambro Engström AB, Bromma, Sweden

[21] Appl. No.: 473,315

[22] Filed: Mar. 8, 1983

[30] Foreign Application Priority Data

Mar. 18, 1982 [SE] Sweden ............................ 8201729

[51] Int. Cl.$^3$ .......................................... A61M 16/00
[52] U.S. Cl. ............................. 128/205.24; 128/910; 128/205.15; 128/205.12
[58] Field of Search .................. 128/205.19, 205.24, 128/204.26, 204.21, 204.23, 203.29, 206.26, 910, 205.25, 205.15, 205.16, 205.12

[56] References Cited

U.S. PATENT DOCUMENTS

| | | |
|---|---|---|
| 3,348,538 | 10/1967 | Benzel ............................ 128/204.26 |
| 3,613,677 | 10/1971 | Blasko ............................ 128/204.21 |
| 3,800,793 | 4/1974 | Manrese et al. .................... 128/910 |
| 4,015,598 | 4/1977 | Brown ................................ 128/203 |
| 4,180,066 | 12/1979 | Milliken et al. ..................... 128/910 |
| 4,219,020 | 8/1980 | Czajka ................................ 128/910 |
| 4,249,528 | 2/1981 | Mathes ............................... 128/910 |
| 4,291,689 | 9/1981 | Hay .................................... 128/910 |
| 4,433,685 | 2/1984 | Giorgini et al. ................ 128/204.26 |

*Primary Examiner*—Henry J. Recla
*Attorney, Agent, or Firm*—Browdy and Neimark

[57] ABSTRACT

An anesthetic apparatus for administering a gaseous anesthetic comprises a breathing mask which is connected to the inspiration pipe and the expiration pipe of the apparatus and used for connecting the apparatus to the airways of a patient. To prevent harmful gaseous anesthetic from being released to the surroundings when the mask is temporarily lifted from the patient's face during anesthesia in order to check the condition of the patient, the apparatus is provided with a gas suction device which can be connected to the mask through a controllable valve. The gas suction device may be continuously operated or may be started automatically when the valve is opened. A signal emitter for generating control signals and applying these to the valve is arranged on, or in the vicinity of the mask in a manner such that it can either be activated manually by the anesthetist, or is activated automatically when the mask is lifted from the patient's face, at which time it generates a control signal for opening the valve. In this way, the suction device is connected with both the inspiration pipe of the anesthetic apparatus and with the mask, whereby all gaseous anesthetic supplied through the inspiration pipe is removed by suction, and also at least the major part of the gas exhaled by the patient is caught and removed by suction through the mask. The suction device has a capacity which at least corresponds to, and preferably exceeds, the maximum flow of gaseous anesthetic capable of being delivered by the anesthetic apparatus any one moment in time.

4 Claims, 1 Drawing Figure

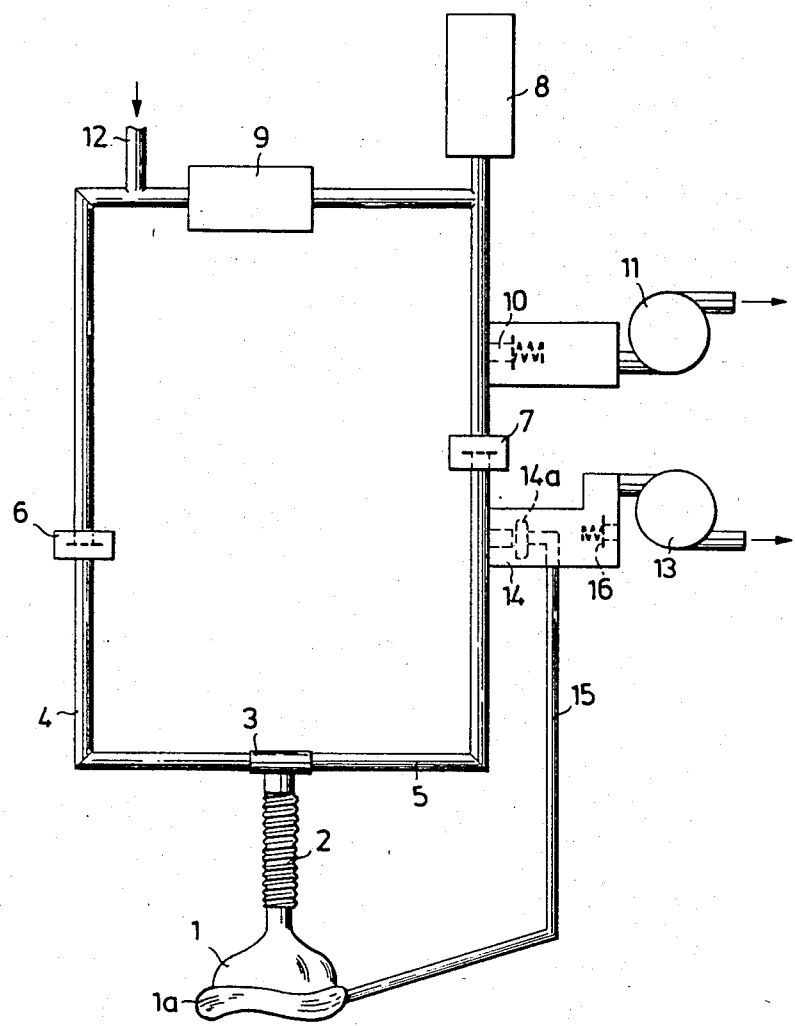

ANESTHETIC APPARATUS

The present invention relates to an anesthetic apparatus equipped with a breathing mask for connecting the airways of a patient to the machine.

In surgical operations when a general anesthetic is required, the anesthetic is, in the majority of instances, only administered over a relatively short period of time, i.e. over a period of less than one hour. In such cases, it is desirable to avoid the use of an endotracheal tube or tracheal cannula inserted in the patient's windpipe. Instead there is used a breathing mask, which is connected to the inspiration and expiration tubes of an anesthetic apparatus through a flexible hose and a Y-piece, and which is arranged to be placed over the mouth and nose of the patient in gas-tight abutment with the face, thereby connecting the anesthetic apparatus to the airways of the patient. Such a breathing mask is generally used to administer anesthetics in such cases, for example, as childbirth, dental treatment and other forms of simple surgery. Normally the patient is able to breath himself, although when administering an anesthetic in this way it is also possible to ventilate the patient mechanically (forced respiration) under the control of the anesthetic apparatus. An anesthetic can be administered through such a breathing mask both in fully open anesthetic systems, in which the whole of the gas expired by the patient through the expiration pipe is removed and rejected, and in fully closed or semiclosed systems, in which the whole or a substantial part of the expired gas is recovered and re-cycled to the patient through the inspiration pipe, subsequent to purifying the expired gas with respect to $CO_2$ and charging said gas with the requisite amount of fresh anesthetic.

When anesthetic is administered through a breathing mask, it is normal practice to lift the mask from the patient's face, to check his or her condition, both during the initial administration of the anesthetic and during the period of continued administration and the awakening period of the patient. This removal of the mask from the patient's face at certain intervals gives rise to a serious problem, since large quantities of gas are released to the surroundings each time the mask is lifted. This released gas comprises partly the anesthetic gas generated by the anesthetic apparatus and delivered through the inspiration pipe and the mask, which gas in a typical case can be delivered, for example, at a rate of 2.7 l/min and may comprise 50–75% nitrous oxide, 0.5–2% halothene and the remainder oxygen, and partly the gas expired by the patient, this gas being at least substantially of the same amount and of the same composition as the gas flowing from the anesthetic apparatus. Consequently, the anesthetist, who is seated close to the patient's head throughout the duration of the anesthesia, is continually exposed to significant quantities of anesthetic gases, which constitutes a serious health risk. In this respect, there has been established an increased frequency in the number of miscarriages and damaged foetus suffered by female anesthetists. Consequently, there is a strong demand for the release of gaseous anesthetics to be either eliminated or at least greatly reduced, in order to improve working hygiene.

With the intention of solving this problem, it has previously been proposed to incorporate in the gas line extending to the breathing mask, i.e. between said mask and said Y-piece, a valve means arranged to be operated manually by the anethetist, the intention being that the anesthetist closes the valve, and holds it closed, when the mask is lifted from the patient's face. This interrupts the flow of anesthetic from the anesthetic apparatus through the breathing mask, and the gas flows instead directly out through the expiration pipe of the apparatus, from which pipe the gas is evacuated in a manner suitable to the design of the anesthetic apparatus used. This solution to the problem, however, is deficient in several ways. For example, approximately half of the total amount of anesthetic gases released still escapes to the surroundings, namely the amount of gas exhaled by the patient. In addition, the necessary, manually operated valve means is relatively large and cumbersome, since in order to avoid excessive resistance to the patient's breathing, the valve must have a low resistance to the flow of gas therethrough. The manually operated valve means makes the work of the anesthetist more difficult, this work being already quite demanding, since it requires great skill and patience to hold the mask tightly against the patient's face.

In view of this, a quite radical solution to the problem has been proposed, this solution requiring the installation of a powerful suction device in the operating theatre, close to the patient's head, this suction device being intended to take up the whole of the gaseous anesthetic which escapes to atmosphere, both from the anesthetic apparatus and from the patient when the mask is lifted from the patient's face. It has been found, that such a suction device should have its inlet opening placed very close to the patient's head, for example at a distance therefrom of about 20 cm, and should have a capacity of about 2000 l/min. This requires a powerful suction fan to be permanently installed in the operating theatre, and the provision of a large-gauge suction pipe, having a diameter of about 10–15 cm. The suction force is so strong as to require a net to be placed over the mouth of the suction pipe, to prevent objects from being sucked thereinto. Naturally, the suction force around the patient's head is also very powerful. It will be understood that this solution to the problem has so many serious disadvantages as to render it generally unacceptable.

Accordingly, the object of the present invention is to provide an anesthetic apparatus of the aforementioned kind, which is so constructed as to practically fully eliminate the escape of gaseous anesthetic to the surroundings when administering said anesthetic through a breathing mask.

The object is realised in accordance with the invention in a simple and effective manner by means of an anesthetic apparatus having the characteristic features disclosed in the following claims.

So that the invention will be more readily understood and further features thereof made apparent an exemplary embodiment of an anesthetic apparatus according to the invention will now be described in more detail with reference to the accompanying drawing.

The single FIGURE of the drawing illustrates, highly schematically, a closed anesthetic apparatus provided with a breathing mask 1 which is connected to the inspiration pipe 4 and the expiration pipe 5 of the apparatus through a flexible hose 2 and a so-called Y-piece 3. The inspiration pipe 4 and expiration pipe 5 incorporate an inspiration valve 6 and an expiration valve 7 respectively, which are controlled in some suitable conventional manner. The expiration pipe 5 is connected to the ventilator unit 8 of the anesthetic apparatus and, via a $CO_2$-absorber 9, also to the inspiration pipe 4. The $CO_2$-absorber 9 is arranged to remove any $CO_2$ present in the gas expired by the patient through the expiration pipe 5. The ventilating unit 8 controls, in a conventional manner, the supply of gaseous anesthetic administered to the patient at mechanical mandatory ventilation of the patient, and contains a supply of anesthetic sufficient for the patient when said patient breathes spontaneously. The expiration pipe 5 is also provided, in a conventional manner, with a spring-loaded overflow valve 10, through which any surplus anesthetic is automatically released; any surplus anesthetic present results in the creation of an over-pressure in the anesthetic circuit, causing the overflow valve 10 to open. The surplus anesthetic released is removed by means of a fan or some other suction means 11 in such a manner as not to cause an anesthetic discharge dangerous to the environment. The inspiration pipe is also provided with an inlet 12 for supplying fresh gaseous anesthetic in a suitable and conventional manner, not shown, for replacing the amount of anesthetic taken up by the patient and released through the overflow valve 10, respectively.

In the aforementioned respects, the anesthetic apparatus is of conventional design, and hence a detailed description of its construction and operational mode in this regard will not be given. As beforementioned, the anesthetic apparatus may also be of another, conventional design, for example may have a fully open patient circuit, in which no part of the gas expired by the patient is recycled to the inspiration pipe.

In order to eliminate the discharge of gaseous anesthetic when the mask 1 is lifted from the patient's face, the anesthetic apparatus according to the invention is provided with a suction device 13, which in the illustrated embodiment comprises a fan means. This suction device is connected to the expiration pipe 5 through a controllable valve 14. The valve 14 is arranged to be closed when the mask 1 is positioned over the patient's mouth and nose, and hence the suction device 13 is unable to affect the function of the anesthetic apparatus during these circumstances. However, when the mask 1 is lifted from the patient's face, at which time there is a risk of anesthetic being released to the surroundings, it is the intention to supply a control signal to the valve 14 so that the valve is opened, thereby placing the suction device 13 in direct communication with expiration pipe 5, and thereby also with the inspiration pipe 4 and the mask 1. The suction device 13 may be designed to be continuously in operation when using the anesthetic apparatus, or to be automatically started at the same time as the valve 14 is opened and to be stopped when the valve 14 closes. The suction device 13 is dimensioned to have a capacity which at least corresponds to, and preferably exceeds the largest flow of gaseous anesthetic which can be delivered from the anesthetic apparatus to the inspiration pipe 4 at any one time under any conditions. It should be observed in this context that this maximum flow of gaseous anesthetic through the inspiration pipe 4 will be present only for a very short duration during each inspiration phase of the patient, when the anesthetic apparatus is adjusted to operate with mechanical mandatory ventilation of the patient. The fan 13 may, for example, have a capacity of about 100 l/min., while typical values for the average inspiration volume, or minute volume, of a patient is 2.7 l/min. It will be seen that when the valve 14 is open and the suction fan 13 is in operation, the fan will withdraw by suction the whole of the flow of gaseous anesthetic delivered by the anesthetic apparatus through the inspiration pipe 4, so that none of this gas flow can be released through the mask 1 when the mask is lifted from the patient's face. Since, in addition, the capacity of fan 13 always, or at least during a major part of the time, substantially exceeds the flow of gas through the inspiration pipe 4 at any given moment, the fan 13 will also create a strong suction force through the mask 1, which will thus function as a suction nozzle, removing all, or at least a greater part of the gas being exhaled by the patient. This completely eliminates the escape of gaseous anesthetic from the anesthetic apparatus, and also greatly reduces the extent to which gaseous anesthetic is discharged from the patient to the surroundings when the mask 1 is lifter from the the patient's face. The gaseous anesthetic withdrawn by suction is led away from fan 13 in some suitable manner, so as to prevent the gas from being discharged in a manner detrimental to the surroundings. As will be understood, it is possible to use, to advantage, a common suction device, for example a fan, for connection to the overflow valve 10 and the controlled valve 14. In this case, the common fan may be arranged to operate at a lower capacity, when the valve 14 is closed and only excess gas need be removed through the overflow valve 10, while the capacity of the fan is automatically increased to the aforementioned necessary high value when the valve 14 is open.

The requisite control of valve 14 can be effected in a number of different ways, depending upon the design of the valve 14 and on whether the valve is to be automatically controlled or manually controlled by the anesthetist.

In the illustrated embodiment, the valve 14 is controlled pneumatically and comprises a so-called pneumatic bladder valve of conventional kind, which contains an elastic pressure chamber or bladder 14a arranged to hold the valve closed under the action of an applied overpressure. This overpressure can be conveniently obtained in the manner illustrated schematically in the drawing, through a pneumatic line 15 which connects the pressure chamber 14a of the valve to the hollow, air-filled sealing bead 1a, often arranged around the abutment edge of the breathing mask 1 to provide a better seal between the mask and the patient's face. When the mask 1 is pressed tightly against the patient's face, the sealing bead 1a is compressed, causing the pressure of the air in said bead to be increased and the valve 14 to be held closed under the action of this overpressure. When the mask 1 is lifted away from the patient's face, the pressure of the air in the sealing bead 1a falls, causing the valve 14 to be opened automatically in the manner desired.

The requisite pressure signals for controlling a pneumatically controlled valve can also be produced by connecting the valve to a pneumatic circuit, to which gas is constantly supplied and which is provided with a vent through which the infed gas can leak out, so as to hold the pressure in the circuit at a low value. If the vent is placed in the proximity of the mask 1, so that it can be held manually closed by the anesthetist, or located in the abutment edge of the mask, so that it is automatically closed when the mask is pressed against the patient's face, a requisite pressure signal can be obtained in the pneumatic circuit for opening and closing the valve 14, since the pressure in the pneumatic circuit will rapidly increase when the vent is closed.

If the valve 14 is, instead, an electrically controlled valve, the requisite control signal can be obtained with the aid of an electric signal emitter, e.g. a switch, arranged on or close to the breathing mask 1 in a manner such that it can be activated either manually by the anesthetist or automatically when the mask is pressed against the patient's face. Such a switch may be very small and readily operated, for example may comprise a touch activated capacitance switch.

The valve 14 may also be controlled opto-electrically, the requisite control signal being supplied to the valve via a fibre optic conductor extending from the breathing mask 1 or from a location in the vicinity of said mask. In this respect, the input end of the fibre optic conductor may be so arranged on the mask 1 as to be readily covered with one of the anesthetist's fingers, or so that it is automatically covered with the mask is pressed against the patient's face.

Irrespective of the design of the valve 14 and manner in which it is controlled, the means for generating the requisite signal for controlling the valve is arranged in the vicinity of the mask 1 or on the mask itself, so as to be readily activated manually by the anesthetist or automatically when the mask is pressed against or lifted from the patient's face, respectively.

As beforementioned, the signal used to control the valve 14 can also be used, either directly or indirectly, for controlling the function of the suction device 13, when said device is not kept running continuously while the anesthetic apparatus is being used.

Although not shown on the drawing, there is suitably provided an alarm or indicating means arranged to produce a signal, for example an acoustic or optic signal, when the valve 14 is open. In this way, the anesthetist is given an alarm should the valve 14 for some reason, for example through malfunctioning, remain open even when the mask is pressed against the patient's face. If the valve 14 should remain open in this position, the patient would receive no gas from the anesthetic apparatus, since all gas supplied from the pipe 14 would be sucked out by the suction device 13. In order to avoid the creation of harmful sub-pressures in the airways of the patient, should the valve 14 malfunction, a sub-pressure valve 16 is suitably arranged in the connection between the suction device 13 and the valve 14, said sub-pressure valve 16 being arranged automatically to open communication with the surrounding atmosphere when a sub-pressure exceeding a given value, for example 1-2 cm $H_2O$, should occur.

In the illustrated embodiment, the suction device 13 is connected, via the controllable valve 14, to the expiration pipe of the machine 1, between the Y-piece 3 and the expiration valve 7. This is considered to be a suitable location for connecting the suction device 13, since it provides a direct connection between the suction device 13 and the mask 1 with but a low resistance to the flow of gas therethrough. The suction device 13, however, could also be connected, via the controllable valve 14, to other locations in the anesthetic circuit, for example to the inspiration pipe 4, between the inspiration valve 6 and the Y-piece 3; the only essential point being that the suction device 13 is connected to the mask 1 as directly as possible, when the valve 14 is open.

We claim:

1. An anesthetic apparatus comprising an inspiration line and an expiration line, a breathing mask connected to one end of said inspiration line and said expiration line respectively, and adapted for placement over the face of a patient for connecting the airways of the patient to said inspiration and expiration lines, a ventilator unit connected to the opposite ends of said inspiration and expiration lines for supplying gaseous anesthetics to said inspiration line and for receiving gas exhaled by the patient from said expiration line, an inspiration valve in said inspiration line permitting a gas flow only in a direction towards said breathing mask, an expiration valve in said expiration line permitting a gas flow only in a direction away from said breathing mask, a gas suction device having a capacity at least corresponding to the greatest flow of gas which said ventilator unit can supply to said inspiration line at any given time, said gas suction device including a suction side through which suction may be applied, valve means connecting the suction side of said gas suction device to one of said expiration and inspiration lines at a point closer to said breathing mask than said expiration valve and inspiration valve respectively, control means for operating said valve means between a closed state and an open state in response to the position of said breathing mask relative to the face of the patient so that said valve means is in said closed state when the breathing mask is pressed against the face of the patient and is in said open state when said breathing mask is lifted from the face of the patient.

2. An apparatus as claimed in claim 1, wherein said control means for said valve means include pneumatic means responsive to a pneumatic control pressure so as to hold said valve means in said closed state when said pneumatic control pressure exceeds a predetermined value and to release said valve means to said open state when said pneumatic control pressure is lower than said predetermined value.

3. An apparatus as claimed in claim 2, wherein said breathing mask is provided with a hollow, air-filled sealing bead along the edge of the mask intended to abut the face of the patient, a pneumatic line being connected between said sealing bead and said pneumatic control means for conveying the air pressure within said sealing bead as said pneumatic control pressure to said pneumatic control means.

4. An apparatus as claimed in claim 1, comprising an under-pressure valve connected to the suction side of said suction device between said valve means and said suction device for connecting the suction side of the suction device to the ambient atmosphere, if the pressure on the suction side of the suction device falls below a predetermined minimum value.

* * * * *